United States Patent
Foster

(10) Patent No.: US 8,550,975 B2
(45) Date of Patent: Oct. 8, 2013

(54) HEART ASSIST APPARATUS

(75) Inventor: Graham Foster, Swansea (GB)

(73) Assignee: Calon Cardio Technology Limited, Swansea (GB)

( * ) Notice: Subject to any disclaimer, the term of this patent is extended or adjusted under 35 U.S.C. 154(b) by 334 days.

(21) Appl. No.: 13/055,581

(22) PCT Filed: Jul. 27, 2009

(86) PCT No.: PCT/GB2009/050927
§ 371 (c)(1),
(2), (4) Date: Jan. 24, 2011

(87) PCT Pub. No.: WO2010/010407
PCT Pub. Date: Jan. 28, 2010

(65) Prior Publication Data
US 2011/0124950 A1  May 26, 2011

(30) Foreign Application Priority Data

Jul. 25, 2008 (GB) .................................. 0813603.8

(51) Int. Cl.
*A61M 1/12* (2006.01)
(52) U.S. Cl.
USPC .......................................................... 600/16
(58) Field of Classification Search
USPC .................................... 600/16–18
See application file for complete search history.

(56) References Cited

U.S. PATENT DOCUMENTS

| 5,147,388 A | * | 9/1992 | Yamazaki .................... 623/3.13 |
| 5,376,114 A | * | 12/1994 | Jarvik ............................ 623/3.3 |
| 5,507,629 A | | 4/1996 | Jarvik |
| 5,824,070 A | * | 10/1998 | Jarvik .......................... 623/3.13 |
| 6,245,007 B1 | * | 6/2001 | Bedingham et al. ............. 600/16 |
| 6,302,910 B1 | * | 10/2001 | Yamazaki et al. .............. 623/3.1 |
| 6,942,611 B2 | * | 9/2005 | Siess ............................... 600/16 |
| 7,048,681 B2 | * | 5/2006 | Tsubouchi et al. ............. 600/16 |
| 8,333,686 B2 | * | 12/2012 | Marseille et al. ............... 600/16 |
| 2009/0203957 A1 | * | 8/2009 | LaRose et al. .................. 600/18 |
| 2010/0249486 A1 | * | 9/2010 | Bar Nathan et al. .......... 588/309 |

FOREIGN PATENT DOCUMENTS

| EP | 0445782 A1 | 9/1991 |
| WO | 2004101029 A1 | 11/2004 |

* cited by examiner

*Primary Examiner* — Kennedy Schaetzle
(74) *Attorney, Agent, or Firm* — Larson & Anderson, LLC

(57) ABSTRACT

The apparatus for implantation into a human heart comprises a pump (1) having an electrical motor (12), an inlet (9) for blood to be located in a first chamber of the heart; an outlet (10) for blood to be located in a second chamber of the heart; fixing means (2) for fixing the apparatus to a wall of the heart with the inlet in the first chamber and the outlet in the second chamber, an elongate conduit (7) which extends from the fixing means to the pump, and an electrical conductor (18) for connecting to the motor, the conductor extending along the conduit.

8 Claims, 2 Drawing Sheets

HEART ASSIST APPARATUS

Figure 1:
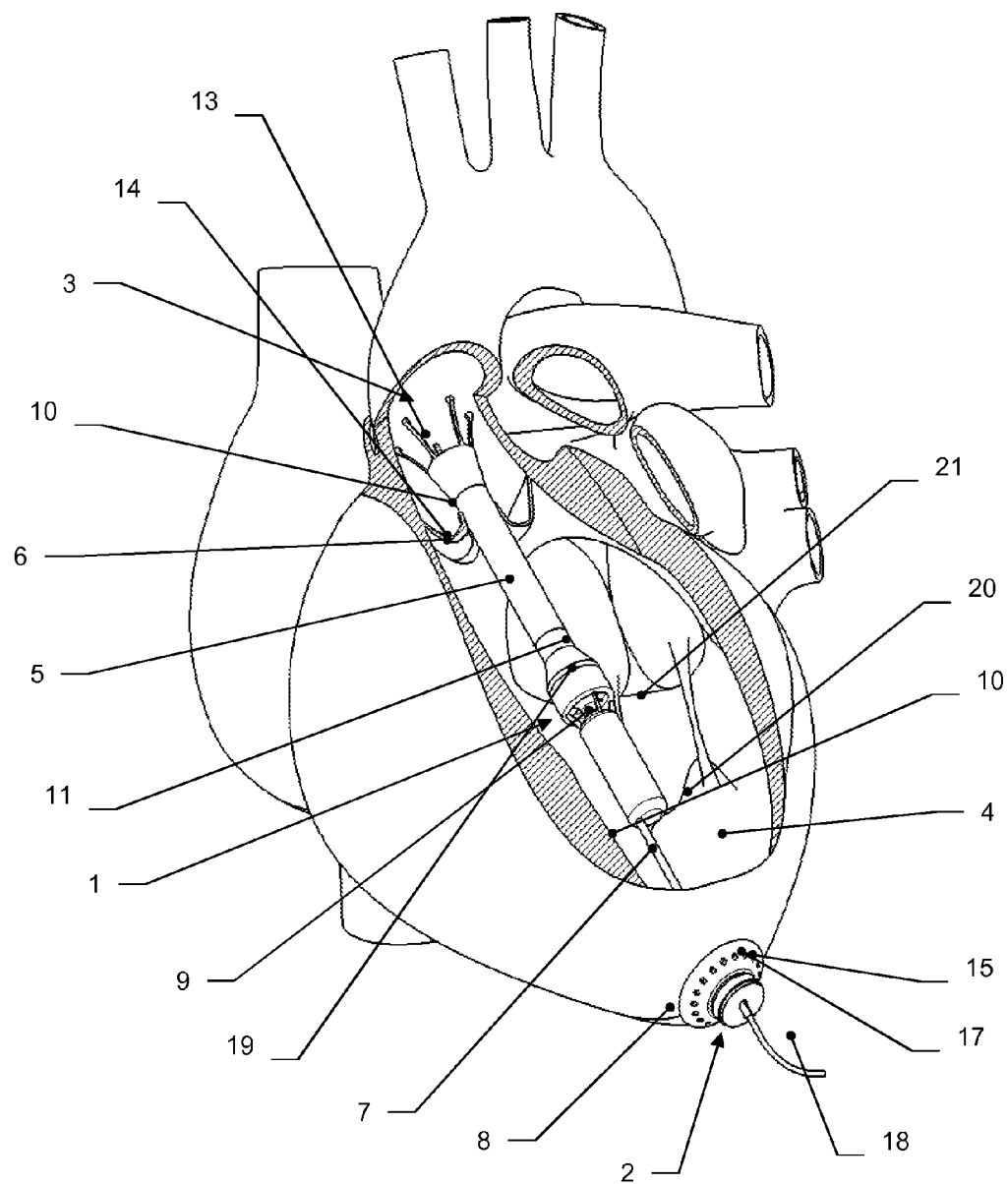

This application is the national stage of PCT/GB2009/050927 filed Jul. 27, 2009, which claims priority to GB0813603.8 filed on Jul. 25, 2008, which are incorporated by reference.

The present invention concerns heart assist apparatus suitable for implantation into the human heart to assist hemodynamic function thereof.

Heart failure is major global health problem resulting in many thousands of deaths each year. Until recently the only way to curatively treat advanced stage heart failure has been by heart transplant or the implantation of a total mechanical heart. Unfortunately donor hearts are only able to meet a tiny fraction of the demand and total mechanical hearts have yet to gain widespread acceptance due to the technical difficulties involved with these devices.

Ventricle assist devices (VADs) have been gaining increased acceptance over the last three decades primarily as a bridge to transplant devices. The devices are implanted long term and work alongside a diseased heart to boost its output and keep the patient alive and/or give a better quality of life whilst awaiting transplant. The use of these devices has had an unexpected result in some patients: the reduction in strain on the heart over a period of time has led to significant spontaneous recovery of the left ventricle. This gives hope to many patients for whom a donor heart may not become available as it could be the case that the early implantation of a VAD may allow their condition to recover before the disease reaches the most advanced stages. It is also a far more preferable outcome to have one's own heart recover rather than undergo a transplant, even if donor hearts are available.

At present, the main reason preventing VADs from being fitted on a more routine basis is the highly invasive surgical procedure required to fit the devices. Typically a sternotomy, full heart lung bypass, and major procedures to the heart and thoracic aorta are required to fit a VAD. Presently the expense and risk of such an operation cannot be justified except in the case of those in the most advanced stages of Heart Failure. If the long term implantation of a VAD or an equivalent circulatory assist device (CAD) could be achieved with a less invasive surgical procedure, ideally eliminating the need for a sternotomy and heart lung bypass, then the use of CADs to treat heart failure in its earlier stages could become far more widespread and routine.

The key to a less invasive implantation procedure for a CAD is to make the device as small as possible so that it can be implanted using a 'keyhole' type procedure.

Furthermore, the method of fixing the device in the implanted destination must also require the minimum of surgical intervention, both during initial implantation and eventual removal. Such a fixing system must also be sufficiently secure that all undesirable movement is eliminated and the device remains secure through its working lifetime.

Another important factor is the management of power cable to the device. If, for example, a CAD is implanted directly into the left ventricle then the power cable must be controlled so that it is not free to move and possibly negatively interact with other structures, such as the papillary fibres or the atrio-ventricular valve.

As a result of the above considerations, there exists a need to develop improved ventricular assist devices suitable for implantation into the human heart. In addition, such miniaturised devices desirably include provision for positioning in their implanted destination and suitable means for management of power cables or similar ancillaries.

According to the invention therefore, there is provided heart assist apparatus suitable for minimally invasive implantation into the human heart, the apparatus comprising a pump having an electrical motor therefor;
an inlet for blood to be located in a first chamber of the heart;
an outlet for blood to be located in a second chamber of the heart;
fixing means for fixing the apparatus to a wall of the heart with the inlet in the first chamber and the outlet in the second chamber,
an elongate conduit which extends from the fixing means to the pump, and
an electrical conductor for connection to the motor, the conductor extending along the conduit.

References to first and second chambers of the heart include a major blood vessel in direct and close communication with the respective chamber. For example, when the chamber is the left ventricle, it will be understood that any reference to the term "chamber" also includes that part of the aorta immediately adjacent to the left ventricle Typically the apparatus according to the invention would reside in the left ventricle of the heart and would operate as a left ventricle assist device (LVAD), although it may be adapted to support other chambers of the heart. In an LVAD configuration the pump would operate across the aortic valve with an inlet to the pump residing in the left ventricle and an outlet of the pump residing in the aorta.

The pump used in the apparatus according to the invention is preferably of an axial flow rotary type, powered by an integrated electric motor. However, other types or configurations of pump may be used, provided they can be suitably miniaturised appropriately for cardiac implantation.

The fixing means is preferably arranged to fix the apparatus to the apex of the left ventricle and is preferably at a first end of the apparatus according to the invention, longitudinally spaced from a second end.

In a preferred embodiment of the invention, the fixing means is arranged to extend through the apex of the ventricle and is provided with a cuff and sealed ring for attachment to the apex of the ventricle. Such a cuff should be arranged to surround the conduit and seal the latter to the respective wall of the heart.

Generally the fixing means is spaced from the pump and/or from the electric motor by the conduit, which provides and defines spacing between the pump (typically the motor of the pump) and the fixing means.

The conduit may be hollow or tubular, in order to carry the electrical conductor internally of the conduit to an electric motor provided in the pump. In the latter embodiment, the conductor is preferably wholly encompassed by the conduit leaving no part thereof exposed to the chamber in which the conduit is located. Alternatively the conduit may be provided with external formations for receiving the conductor. The conductor is typically an insulated an insulated power cable or the like.

In a particularly preferred embodiment of the invention, the conduit is flexible or semi-rigid (that is, it is preferred that the conduit is not wholly rigid). It is further preferred that the conduit can bow laterally; that is, it can deform laterally more readily than it can deform longitudinally.

The conduit may be made of a material which is inherently flexible, such as a biocompatible plastics material (examples of which include polypropylene and polytetrafluoroethylene) . Alternatively, the conduit may be flexible as a result of its mechanical structure. In the latter case, the conduit may be formed in the manner of a helical spring, or it may have preformed formations permitting bending at predetermined locations. Such a conduit may, for example, be of biocompatible metal.

The conduit extends as a tail from the pump to the fixing means. Such a flexible conduit preferably has flexibility sufficient to accommodate misalignment of opposed ends of the apparatus caused by the beating of the heart. However, the degree of flexibility should be limited so that positional integrity of the pump can be maintained.

A further beneficial feature of the conduit is that it can serve to keep the pump and the electrical conductor clear of other structures of the heart, such as, for example, the atrio-ventricular valve and the papillary fibres. The conductor may be enclosed within the conduit (such as a tubular conduit), or it may, for example, be routed along the periphery thereof. The electrical conductor may be for a power supply to the pump and/or for the communication of data to and/or from the pump.

Preferably the conduit is of a substantially smaller external diameter than that of the pump. It can serve to space the pump from the apex of the ventricle.

Preferably a cannula or lumen extends from the pump to the outlet, and it is particularly preferred that the latter cannula, the electric motor, and preferably also the outlet, are all arranged to be longitudinally extending and coaxial with one another.

The outlet is preferably longitudinally spaced from the fixing means.

The outlet may be arranged to attach the apparatus in position in the aorta and centralise the apparatus (in particular, the outlet) across the aortic valve. The outlet is therefore preferably at a second end of the apparatus according to the invention In a preferred embodiment of the invention, the outlet is preferably provided at its end with at least one selectively compressible/expandable formation so that the external diameter at the outlet can be reduced during implantation or removal, in order to allow the expandable formation to pass through a small incision in the apex and the aortic valve. Following such constriction the diameter can then be allowed to increase (typically as a result of resilience of the respective formation) in order to permit the expandable formation to interact or engage with the wall of the aorta in the implanted position (preferably to anchor the end of the outlet in a desired implanted position). The expandable formation used for this purpose may be integral with an outlet of the pump, and may typically comprise one or more outwardly extending legs, or a compressible annular member or the like.

Figure 2:
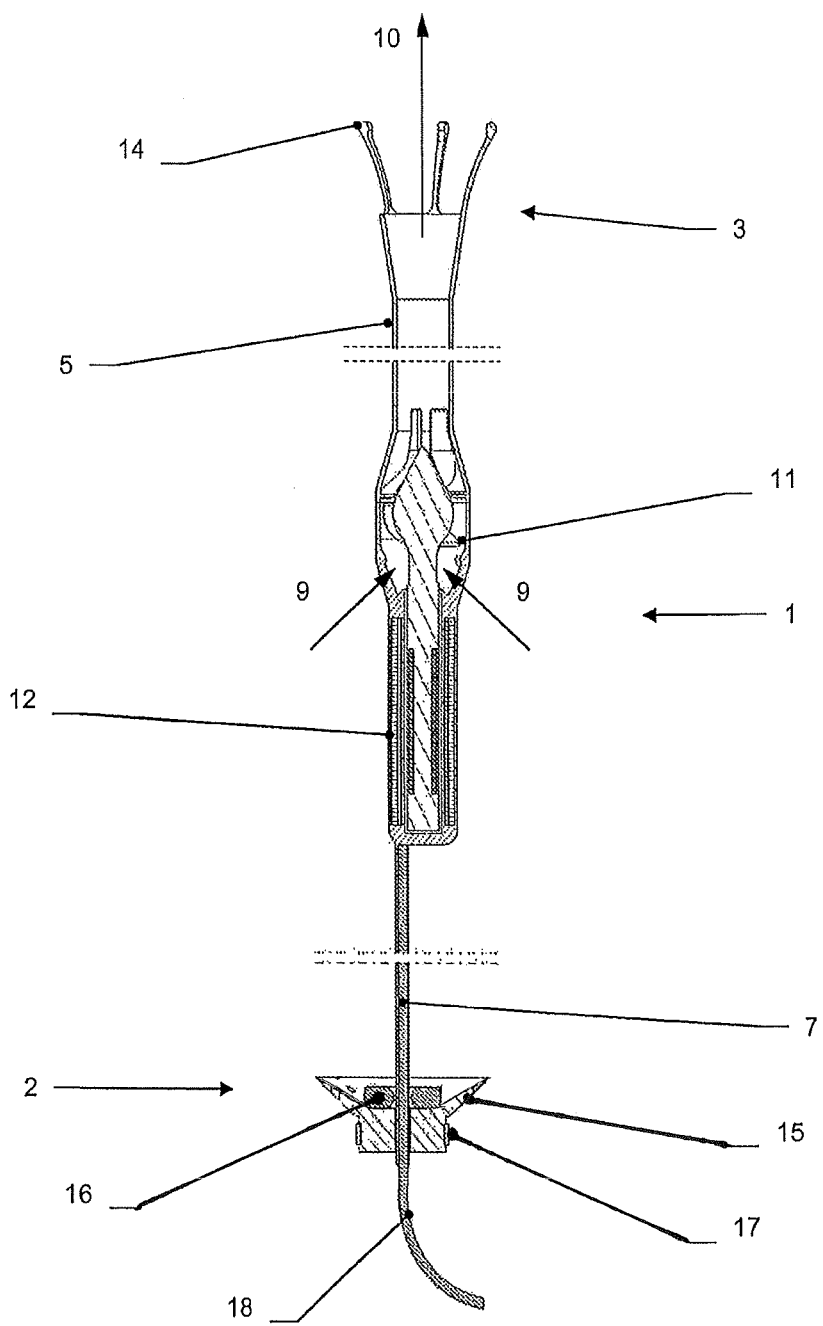

Embodiments of the invention and preferred features thereof will now be described in more detail, with reference to accompanying drawings, in which:

FIG. 1 is a perspective partial cutaway view of a preferred embodiment of a heart assist apparatus according to the invention when implanted into the human heart; and FIG. 2 is a cutaway view of the ventricular assist apparatus shown in FIG. 1.

Referring to both FIGS. 1 and 2, in which like parts are denoted by like reference numerals, there is shown an exemplary heart assist apparatus including a pump body 1, a first fixing end 2, and a second outlet end 3 longitudinally spaced from the first end. In the illustrated embodiment, the pump body 1 is located in the left ventricle 4 of the heart with an outflow cannula or lumen 5 extending across the aortic valve 6 to the second outlet end 3. The first fixing end 2 is attached to the pump body 1 via a conduit or spacing member 7 that extends through the apex 8 of the ventricle 4.

The pump body 1 in the preferred embodiment is an axial flow rotary pump (though other types of suitably miniaturised pump may be used) and comprises (see in particular FIG. 2) an inlet 9 for blood, an outlet 10 for blood (expanded by the cannula 5), a pumping chamber 11 extending from the inlet to the outlet, and a motor portion 12. For effective operation, the inlet 9, or an extension thereof, should reside in the left ventricle 4, while the outlet 10, or an extension thereof, should reside in the aorta 13 so that the pump effectively straddles the aortic valve 6. Although the preferred embodiment shows the main pump body 1 residing in the left ventricle 4, it can be appreciated that its position could be easily changed to be in the aorta 13 or to straddle the aortic valve 6.

The first fixing end 2 is positioned on the apex 8 of the ventricle and is connected to the pump body 1 by the elongate conduit or spacing member 7. The end 2 further includes a cuff 15, a sealing ring or felt 16 and a clamp 17. The cuff 15 is securely fixed to the apex 8 of the ventricle, typically by means of sutures and/or a tissue compatible adhesive, or by other suitable fixing method.

The sealing ring 16 is trapped between the cuff 15 and the apex 8, and there forms a blood-tight seal around the emergence of the conduit or extension member 7 from the apex 8. The conduit or spacing member 7 passes through the centre axis of the sealing ring 16 and cuff 15 and is retained in position by the tightening of the clamp 17 around the cuff 15. The cuff 15 allows sufficient give for the clamping force to be transferred to the conduit or spacing member 7 ensuring it is securely held.

The clamp 17 can take the form of any one of a well known range of clamp types, examples being a band clamp, a cable tie or a crimp ring. The clamp 17 is also preferably releasable.

The second end 3 is adapted to centralise the pump body 1 relative to the aorta 13 and the aortic valve 6, in order to ensure that the valve leaflets seal effectively against the outside of the outlet cannula 5 and also to make sure that the pump 1 does not cause damage to the valve 6 by sitting off centre. In the preferred embodiment, flexible legs 14 extend outwardly (typically radially outwardly) from the outlet 10 and exert a light spring force against the wall of the aorta 13 which is sufficient to centralise the device but not sufficient to cause damage or embedding into the vessel. The flexible legs 14 are also inwardly compressible to enable easy insertion and removal of the device and especially the second end 3.

Whilst the end 3 in the preferred embodiment illustrated is attached or held in place primarily by means of flexible legs 14, other methods of attachment are possible and would remain within the scope of the invention. For example, the flexible legs 14 could be replaced with an expanding stent arrangement similar to those commonly used for blood vessel stenting (a well known and established technology). Alternatively, the legs could be replaced by a hydrophilic biocompatible material which is such that it will swell or expand in situ.

This method to would be well suited for when a long term or permanent implantation is required. It is also possible that end 3 may not have fixing structures but may centralise as a result of the natural centralising effect of the aortic valve 6 on the outlet cannula 5.

In the embodiment illustrated, the conduit or spacing member 7 is tubular and encloses the power cable 18 for the electric motor 12, thus ensuring that the path of the power cable 18 is well managed and does not interfere with other structures of the heart such as the ventricle wall 19, the papillary fibres 20 or the atrio-ventricular valve 21.

The conduit or spacing member 7 is typically of a semi-rigid construction that allows enough flexibility that it can flex or bow relatively easily so as to accommodate for movement resulting from the beating of the heart and from the two ends 2 and 3 not being completely radially aligned. However, the conduit or spacing member 7 should still be rigid enough to ensure that the position of the pump body 1 is stable and in particular that the outlet cannula 5 remains coaxially aligned with the aortic valve 6 in use of the apparatus.

In other words, the movement allowed by the construction of the conduit or spacing member 7 should be greater in a direction perpendicular to the longitudinal axis of the conduit or spacing member 7 than it is in a direction along the longitudinal axis of the spacing conduit or spacing member 7.

A surgical procedure to fit the apparatus according to the invention would typically comprise the following steps:

a mini thorachotomy is used to gain access to the apex 8 of the ventricle; traction is then placed on the heart to stabilise it positionally;

a small incision is then made in the apex 8 (note that this would be carried out whilst the heart is still functioning—bypass is not required);

the apparatus is then introduced into the heart through the incision via a cannula to contain the end 3 that resides in the aorta 13 (or alternatively a sheath which can be split could be used);

the apparatus is then positioned correctly relative to the aortic valve 6;

the incision in the apex 8 is then sutured closed around the conduit or spacing member 7;

the sealing ring 16 and cuff 15 are then slid into position over the conduit or spacing member 7;

the cuff 15 is then attached to the apex 8;

the clamp 17 is then tightened setting the position of the apparatus;

the power cable 18 is then routed to a suitable exit point (or to an implantable inductive coil); and then the initial thorachotomy is closed.

The above procedure, made possible by the design of the apparatus according to the invention, represents a significant reduction in surgical trauma required to fit a circulatory assist device compared to current technology.

Overall, the use of the apparatus according to the invention provides a solution to the minimally invasive implantation of a miniaturised pump into the human heart, taking into account the need to position the apparatus and manage the routing of any power lead for the pump.

The invention claimed is:

1. Heart assist apparatus suitable for implantation into the human heart, the apparatus comprising
   (a) a pump having an electrical motor therefor;
   (b) an inlet for blood, said inlet adapted to be located in a first chamber of the heart;
   (c) an outlet for blood, said outlet to be located in a second chamber of the heart;
   (d) a fixture for fixing the apparatus to a wall of the heart with said inlet in said first chamber and said outlet in said second chamber;
   (e) an elongate conduit which extends from the fixture to the pump, the conduit being sufficiently flexible to allow movement of the pump relative to said fixture, and
   (f) an electrical conductor for connection to the motor, said conductor extending along said conduit.

2. Apparatus according to claim 1, where the conduit encloses said electrical conductor.

3. Apparatus according to claim 1, in which the inlet is connected to the outlet by a cannula.

4. Apparatus according to claim 3, in which the outlet is integral with the cannula.

5. Apparatus according to claim 1, wherein the fixture is arranged to attach to the apex of the ventricle and is further provided with a sealing ring or felt, and a cuff arranged to form a blood-tight seal around the conduit.

6. Apparatus according to claim 5, further comprising a clamp for clamping the cuff to the apex.

7. Apparatus according to claim 1, wherein the pump is of an axial flow rotary type.

8. Apparatus according to claim 1, wherein the elongate conduit has an effective outside diameter smaller than that of the pump.

\* \* \* \* \*